US012207795B2

(12) United States Patent
Purohit et al.

(10) Patent No.: US 12,207,795 B2
(45) Date of Patent: Jan. 28, 2025

(54) MEDICAL SYSTEMS, DEVICES AND RELATED METHODS

(71) Applicant: Boston Scientific Medical Device Limited, Galway (IE)

(72) Inventors: Hitendra Purohit, New Delhi (IN); Agrim Mishra, New Delhi (IN); Nitesh G. Baviskar, Maharashtra (IN); Rohit Bhardwaj, Kurukshetra (IN); Saniya Kshirsagar, Maharashtra (IN); Sharath Kumar G., Kanakapura (IN); Swami Upadhyay, Raipur (IN)

(73) Assignee: Boston Scientific Medical Device Limited, Galway (IE)

( * ) Notice: Subject to any disclaimer, the term of this patent is extended or adjusted under 35 U.S.C. 154(b) by 411 days.

(21) Appl. No.: 17/342,918

(22) Filed: Jun. 9, 2021

(65) Prior Publication Data

US 2021/0386273 A1    Dec. 16, 2021

Related U.S. Application Data

(60) Provisional application No. 63/037,862, filed on Jun. 11, 2020.

(51) Int. Cl.
*A61B 1/005* (2006.01)
*A61B 1/01* (2006.01)
*A61B 1/018* (2006.01)

(52) U.S. Cl.
CPC .......... *A61B 1/0052* (2013.01); *A61B 1/0057* (2013.01); *A61B 1/01* (2013.01); *A61B 1/018* (2013.01); *A61B 2217/007* (2013.01)

(58) Field of Classification Search
CPC ..... A61B 1/005; A61B 1/0051; A61B 1/0052; A61B 1/0053; A61B 1/0055;
(Continued)

(56) References Cited

U.S. PATENT DOCUMENTS 5,075,062 A * 12/1991 Karpiel ................. A61B 18/14
264/238
5,810,807 A * 9/1998 Ganz ................. A61B 18/1492
606/113

(Continued)

FOREIGN PATENT DOCUMENTS

RU    2608440 C2    1/2017

OTHER PUBLICATIONS

International Search Report, dated Sep. 8, 2021, in application PCT/IB2021/055073 (4 pages).

*Primary Examiner* — Ryan N Henderson
(74) *Attorney, Agent, or Firm* — Bookoff McAndrews PLLC (57) ABSTRACT

In one example, a medical device may include a handle including a proximal portion and a distal portion, and the proximal portion may pivot relative to the distal portion. The medical device may also include an insertion portion coupled to the distal portion of the handle and configured to be positioned within a body lumen; and an articulation wire extending from the handle through the insertion portion. Pivoting of the proximal portion of the handle relative to the distal portion of the handle may move the articulation wire relative to the insertion portion to bend a distal portion of the insertion portion.

20 Claims, 7 Drawing Sheets

(58) Field of Classification Search
CPC ... A61B 1/0056; A61B 1/0057; A61B 1/0058; A61B 1/008; A61B 1/00087; A61B 1/0014; A61B 2017/003; A61B 2017/00318; A61B 2017/00323; A61B 2017/00327; A61M 25/0133; A61M 25/0136; A61M 25/0147

See application file for complete search history.

(56) References Cited

U.S. PATENT DOCUMENTS

| | | | | |
|---|---|---|---|---|
| 6,471,702 | B1* | 10/2002 | Goto | A61B 18/14 |
| | | | | 606/46 |
| 6,817,974 | B2* | 11/2004 | Cooper | A61B 17/00234 |
| | | | | 606/205 |
| 7,708,758 | B2* | 5/2010 | Lee | A61B 17/29 |
| | | | | 606/205 |
| 7,833,223 | B2* | 11/2010 | Vakharia | A61B 18/1492 |
| | | | | 606/113 |
| 8,021,363 | B2* | 9/2011 | Vakharia | A61B 18/1492 |
| | | | | 606/113 |
| 9,138,250 | B2* | 9/2015 | Lu | A61B 17/32056 |
| 9,723,973 | B2* | 8/2017 | Dillon | A61B 1/00066 |
| 9,861,432 | B2* | 1/2018 | Gittard | A61B 18/1492 |
| 11,311,326 | B2* | 4/2022 | Boudreaux | A61B 18/00 |
| 2003/0036748 | A1 | 2/2003 | Cooper | A61B 34/30 |
| | | | | 901/29 |
| 2003/0208219 | A1* | 11/2003 | Aznoian | A61B 17/32056 |
| | | | | 604/95.04 |
| 2004/0015050 | A1* | 1/2004 | Goto | A61B 18/1492 |
| | | | | 600/104 |
| 2005/0272975 | A1* | 12/2005 | McWeeney | A61B 1/307 |
| | | | | 600/172 |
| 2006/0142695 | A1* | 6/2006 | Knudson | A61M 25/0136 |
| | | | | 604/95.04 |
| 2007/0250110 | A1* | 10/2007 | Lu | A61B 17/32056 |
| | | | | 606/205 |
| 2007/0255299 | A1* | 11/2007 | Vakharia | A61B 18/1492 |
| | | | | 606/170 |
| 2007/0293874 | A1* | 12/2007 | Okada | A61B 17/32056 |
| | | | | 606/113 |
| 2008/0046000 | A1* | 2/2008 | Lee | A61B 17/29 |
| | | | | 606/205 |
| 2009/0105534 | A1* | 4/2009 | Nakagawa | A61B 1/018 |
| | | | | 600/106 |
| 2010/0298634 | A1* | 11/2010 | Yanuma | A61B 17/22 |
| | | | | 606/127 |
| 2011/0207999 | A1* | 8/2011 | Torisawa | A61B 1/00078 |
| | | | | 600/114 |
| 2014/0223701 | A1* | 8/2014 | Bean | A61B 1/0014 |
| | | | | 24/483 |
| 2014/0296630 | A1* | 10/2014 | Zwirkoski | A61B 1/0057 |
| | | | | 600/109 |
| 2015/0057537 | A1* | 2/2015 | Dillon | A61B 1/0014 |
| | | | | 600/113 |
| 2015/0297865 | A1* | 10/2015 | Hinman | A61B 1/0055 |
| | | | | 606/1 |
| 2016/0331452 | A1* | 11/2016 | Oguni | A61B 1/018 |
| 2017/0156711 | A1* | 6/2017 | Jogasaki | A61B 1/00 |
| 2018/0289436 | A1* | 10/2018 | Jorgensen | A61B 18/1492 |
| 2020/0077878 | A1* | 3/2020 | Halderman | G02B 23/2423 |
| 2020/0170738 | A1* | 6/2020 | Hasegawa | A61B 34/71 |
| 2021/0386273 | A1* | 12/2021 | Purohit | A61B 1/0057 |
| 2022/0054800 | A1* | 2/2022 | Kimmel | A61M 25/0147 |
| 2023/0000313 | A1* | 1/2023 | Sharma | A61B 1/0055 |
| 2023/0122303 | A1* | 4/2023 | Yanuma | A61B 1/273 |
| | | | | 600/107 |

\* cited by examiner

MEDICAL SYSTEMS, DEVICES AND RELATED METHODS

This application claims the benefit of priority from U.S. Provisional Application No. 63/037,862, filed on Jun. 11, 2020, which is incorporated by reference herein in its entirety.

TECHNICAL FIELD

Aspects of this disclosure generally relate to medical systems, devices, and methods. For example, aspects of this disclosure relate to medical systems, devices, and methods for operating medical devices, such as sphincterotomes.

BACKGROUND

Medical devices, such as endoscopes or other suitable insertion devices, are employed for a variety of types of diagnostic and surgical procedures, such as endoscopy, laparoscopy, arthroscopy, gynoscopy, thoracoscopy, cystoscopy, etc. Many of these procedures involve delivering an insertion device to a position within the body of a patient. Additionally, many procedures involve delivering a medical device through a lumen in the insertion device. In particular, such procedures may be carried out by inserting the insertion device (e.g., a duodenoscope) into a subject's body through a surgical incision, or via a natural anatomical orifice (e.g., mouth, vagina, or rectum), and performing the procedure or operation at a target site with an auxiliary medical device (e.g., a sphincterotome) inserted through the insertion device.

The insertion device and the medical device may each have one or more illumination devices (e.g., LEDs), visualization devices (e.g., cameras), etc., which require power sources, display devices, etc. The medical device may rely on the maneuverability of the insertion device in order to position the medical device at a target region. Limited indirect control of the medical device through movement of the insertion device may increase the duration, costs, training time, and risks of the medical procedure.

The devices and methods of this disclosure may rectify some of the deficiencies described above or address other aspects of the prior art.

SUMMARY

Examples of this disclosure relate to, among other things, systems and devices for coupling and controlling medical devices, performing one or more medical procedures with the medical devices, and related methods of use thereof, among other aspects. Each of the examples disclosed herein may include one or more of the features described in connection with any of the other disclosed examples.

In one example, a medical device may include a handle including a proximal portion and a distal portion, and the proximal portion may pivot relative to the distal portion. The medical device may also include an insertion portion coupled to the distal portion of the handle and configured to be positioned within a body lumen; and an articulation wire extending from the handle through the insertion portion. Pivoting of the proximal portion of the handle relative to the distal portion of the handle may move the articulation wire relative to the insertion portion to bend a distal portion of the insertion portion.

The medical device may include one or more of the following features. The medical device may further include: a cautery wire extending through the insertion portion; and an actuator positioned on the handle and configured to supply energy from an energy source to the cautery wire. The articulation wire may be a first articulation wire, the device may further include a second articulation wire extending from the handle through the insertion portion; and an actuator positioned on the handle, wherein the second articulation wire is configured to move a distal portion of the insertion portion when the actuator is actuated. The handle may be a first handle, and further include a mounting clamp configured to couple the first handle to a second handle of a second medical device, wherein the mounting clamp includes a first clamp, a second clamp, and an arm extending between the first clamp and second clamp, wherein the arm is configured to space the first handle from the second handle. The insertion portion may include an irrigation lumen, a guidewire lumen, and a cautery lumen accommodating a cautery wire. The handle may be coupled to the insertion portion via a rotatable coupling assembly; and wherein the handle is configured to move the articulation wire by pivoting about the rotatable coupling assembly.

The medical device may include one or more of the following features. The articulation wire may be a first articulation wire and the rotatable coupling assembling may include a first gear at a distal end of the proximal portion of the handle; a second gear engaged with the first gear, wherein the first articulation wire is coupled to the second gear; and a third gear engaged with the first gear, wherein a second articulation wire is coupled to the third gear. The articulation wire may be a first articulation wire and the rotatable coupling assembling may include a pair of flanges coupled to the proximal portion of the handle; a first cam, wherein the first articulation wire is coupled to the first cam; and a second cam, wherein a second articulation wire is coupled to the second cam, and wherein the pair of flanges engages the first cam and the second cam to cause movement of the first articulation wire and the second articulation wire, respectively. The articulation wire may be a first articulation wire and the rotatable coupling assembling may include a first gear at a distal end of the proximal portion of the handle; a second gear engaged with the first gear and positioned such that the first gear rotates about a first axis and the second gear rotates about a second axis that extends transverse to the first axis, wherein the first articulation wire is coupled to the second gear; and a third gear engaged with the first gear, wherein the third gear rotates about a third axis that extends transverse to the first axis, and wherein a second articulation wire is coupled to the third gear. The handle may be L-shaped and may include a rotatable coupling assembly configured to directly couple to a port of a second medical device, and wherein the handle is configured to move the articulation wire by pivoting about the rotatable coupling assembly. The handle may be cylindrical, made of a flexible material, and includes a coupler at a distal end of the handle, the coupler may be configured to fixedly couple the handle to a port of a second medical device, and a proximal portion of the handle may be configured to bend to move the articulation wire. Clockwise rotation of the first gear may result in counter-clockwise rotation of the second gear and the third gear; counter-clockwise rotation of the second gear may cause proximal movement of the first articulation wire; and counter-clockwise rotation of the third gear may cause distal movement of the second articulation wire.

In some examples, the medical device may include one or more of the following features. The first gear may be proximal to the second gear and the third gear; the second gear and the third gear may be positioned on opposing sides of a central longitudinal axis of the handle; and the proximal portion of the handle may pivot about a center of the first gear. Pivoting of the proximal portion of the handle may cause a first flange or a second flange of the pair of flanges to move at least one of the first cam or the second cam proximally and move at least one of the first articulation wire or the second articulation wire proximally, and wherein the first cam and the second cam each have a pivot axis proximal to the pair of flanges. Pivoting the proximal portion of the handle in a first direction may cause 1) a first flange to move the first cam proximally and 2) a second flange to move distally and allow the second cam to move distally; and wherein pivoting the proximal portion of the handle in a second direction causes 1) the second flange to move the second cam proximally and 2) the first flange to move distally and allow the first cam to move distally.

In another example, the medical device may include a handle; an insertion portion coupled to the handle and configured to be positioned within a body lumen; and a first articulation wire and a second articulation wire each extending through the insertion portion and having a proximal end coupled to the handle and a distal end coupled to a distal end of the insertion. The handle may include a coupler, the coupler comprising one of first and second gears or first and second cams, wherein the first and second articulation wires are respectively coupled to the one of the first and second gears or the first or second cams; wherein pivoting of a portion of the handle relative to the coupler translates at least one of the first articulation wire and the second articulation wire to bend the distal end of the insertion portion.

The medical device may include one or more of the following features. The coupler may include the first and second gears, and wherein the handle may include a third gear, wherein pivoting of a portion of the handle relative to the coupler causes the third gear to move the first and second gears simultaneously. The coupler may include the first and second cams, and the handle may include a pair of flanges that are configured to move the first cam and the second cam when the handle is pivoted relative to the coupler.

In yet another example, a method may include inserting a distal portion of an first insertion portion of an insertion device into a patient body, wherein the insertion device includes a first handle coupled to the first insertion portion; coupling a second handle of a medical device to the first handle, wherein the medical device includes a second insertion portion coupled to the second handle of the medical device; inserting the second insertion portion of the medical device through a lumen of the insertion device and into the patient body; and moving a distal portion of the second insertion portion via pivoting the second handle relative to another portion of the medical device. The method may further include moving a distal portion of the second insertion portion via actuating an actuator of the second handle.

It may be understood that both the foregoing general description and the following detailed description are exemplary and explanatory only and are not restrictive of this disclosure, as claimed.

BRIEF DESCRIPTION OF THE DRAWINGS

The accompanying drawings, which are incorporated in and constitute a part of this specification, illustrate exemplary aspects of this disclosure and together with the description, serve to explain the principles of this disclosure.

DETAILED DESCRIPTION

Examples of this disclosure include devices and methods for facilitating and improving the efficacy, efficiency, and/or safety of operating a medical device during a medical procedure, among other aspects. For example, aspects of this disclosure may provide a user (e.g., physician, medical technician, or other medical service provider) with the ability to physically connect and operate two handles of two medical devices (e.g., an insertion device and a medical device). Aspects of this disclosure may also provide the user with the ability to deliver the insertion device to a location within a patient's body, and also deliver the medical device through an internal lumen of the insertion device to the location within the patient's body to, for example, visualize, resect, energize, treat, or otherwise manipulate tissue or material within a patient's body.

Embodiments of this disclosure may relate to systems for performing various medical procedures and methods for accessing the papilla and/or biliary duct and/or any other suitable patient anatomy. Various embodiments described herein may include single-use or disposable medical devices. In exemplary embodiments, the medical system may be configured to deliver and position a visualization device and/or an access device, e.g., a tome such as a sphincterotome, for accessing the papilla of Vater or major papilla. The papilla of Vater generally forms the opening where the pancreatic duct and the common bile duct empty into the duodenum of the small intestine. The hepatic ducts and the gall bladder empty into the common bile duct. An endoscopic or biliary procedure may require advancing a medical device to a suitable location along the biliary tree and then performing the appropriate intervention. The medical devices and methods disclosed herein provide access and visualization (and a delivery system for visualization and access devices) to, among other areas, the papilla and/or pancreatico-biliary system. For example, the insertion device may be a duodenoscope that may be delivered to gain access to a papilla, and the medical device may be inserted through the duodenoscope and extended distally beyond the insertion portion of the duodenoscope and into a biliary duct. In some aspects, the medical devices and methods disclosed herein may be used to perform cannulation or endoscopic sphincterotomy (EST) that are techniques related to endoscopic retrograde cholangiopancreatography (ERCP).

Some aspects of this disclosure may be used in performing an endoscopic, laparoscopic, arthroscopic, or other type of procedure. For example, the disclosed aspects may be used with duodenoscopes, bronchoscopes, ureteroscopes, colonoscopes, catheters, diagnostic or therapeutic tools or devices, or other types of medical devices.

Reference will now be made in detail to examples of this disclosure described above and illustrated in the accompanying drawings. Wherever possible, the same reference numbers will be used throughout the drawings to refer to the same or like parts. The terms "proximal" and "distal" are used herein to refer to the relative positions of the components of an exemplary medical device. When used herein, "proximal" refers to a position relatively closer to the exterior of the body or closer to a medical professional using the medical device. In contrast, "distal" refers to a position relatively further away from the medical professional using the medical device, or closer to the interior of the body. Proximal and distal directions are labeled with arrows marked "P" and "D", respectively, throughout the figures. As used herein, the terms "comprises," "comprising," "having," "including," or other variations thereof, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/− 10% of a stated value.

Figures 1A, 1B:
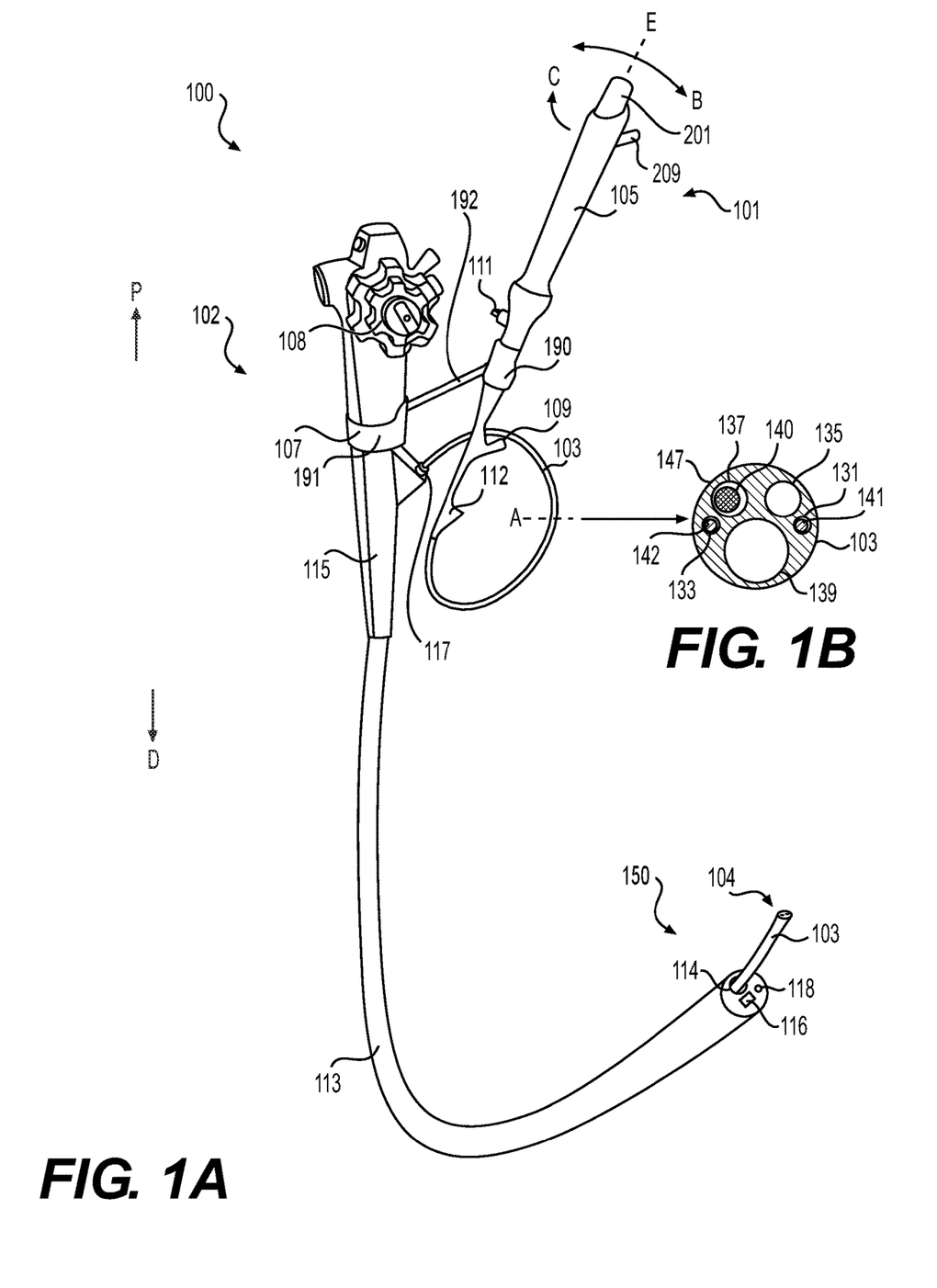
FIG. 1A illustrates an exemplary medical system including two medical devices in a coupled configuration, according to aspects of this disclosure.
FIG. 1B illustrates a cross-sectional view of an exemplary portion of a medical device in FIG. 1A, according to aspects of this disclosure.

FIG. 1A depicts a medical system 100 that includes an insertion device 102 and a medical device 101. FIG. 1A illustrates insertion device 102 and medical device 101 in a coupled configuration. Insertion device 102 may be an endoscope, duodenoscope, bronchoscope, ureteroscope, colonoscope, or other type of medical device. In one aspect, insertion device 102 may be a single-use type medical device. In another aspect, insertion device 102 may be a reusable type medical device. Medical device 101 may be a sphincterotome, another tome catheter, or other type of medical device.

Insertion device 102 may have a handle portion 115 and an insertion portion 113, which may be inserted into a body lumen of a subject during a medical procedure. Insertion portion 113 may be joined to handle portion 115. Handle portion 115 may include one or more actuators 108 for actuating control wires or other features of insertion device 102. A working channel port 117 may be positioned on handle portion 115 and may provide access to a working channel that extends longitudinally through insertion device 102. Working channel port 117 may be used for passing one or more instruments or other devices (e.g., a portion of medical device 101) through a working channel of insertion portion 113 to a distal portion 150 of insertion device 102. In other examples, insertion device 102 may include a plurality of working channels extending longitudinally through insertion portion 113. Distal portion 150 of insertion portion 113 may include one or more cameras 116, one or more illuminators 118, and an opening 114 of the working channel of insertion device 102. The one or more cameras 116 and one or more illuminators 118 may be coupled to a controller within handle portion 115 of insertion device 102 and/or to a control unit (not shown) electronically coupled to insertion device 102. A user may visualize a camera feed from camera 118 using an electronic display (not shown).

Handle portion 115 may include a number of components used by an operator to control insertion device 102 before, during, or after a procedure involving insertion device 102. For example, actuators 108 may be used to control deflection of distal portion 150 of insertion portion 113. In some examples, actuators 108 may include two knobs used for deflecting distal portion 150 of insertion portion 113. One of knobs may be used to deflect distal portion 150 of insertion portion 113 along a first axis, and the other knob may be used to deflect distal portion 150 of insertion portion 113 along a second axis transverse to the first axis. For example, a first knob may be operable to deflect distal portion 150 of insertion portion 113 in a left/right direction, and the other knob may be operable to deflect distal portion 150 of insertion portion 113 in an up/down direction. Although not shown, actuators 108 may also include one or more locking mechanisms, which may be used to limit distal portion 150 of insertion portion 113 from moving in a left/right and/or an up/down direction or otherwise lock the position of the distal portion 150 of insertion portion 113.

Medical device 101 may include an insertion portion 103 and a handle portion 105. As shown in FIG. 1A, handle portion 105 may be coupled to handle portion 115 of insertion device 102 via a mounting clamp 107. Insertion portion 103 be inserted through working channel port 117 and through insertion portion 113 of insertion device 102 such that insertion portion 103 may extend through and distally beyond distal portion 150 of insertion portion 113 and into the body of a subject during a medical procedure. A distal end 104 of insertion portion 103 may be configured to move within the body of a subject during a medical procedure independently of insertion portion 113. Insertion portion 103 may be joined to handle portion 105.

Mounting clamp 107 may include a first clamp 190 configured to couple to handle portion 105, a second clamp 191 configured to couple to handle portion 115, and an arm 192 fixedly coupled to each of the first clamp 190 and the second clamp 191. Second clamp 191 may be positioned on an intermediate position on handle portion 115, for example proximal to the working channel port 117 and distal to actuators 108. Arm 192 may space handle portion 105 from handle portion 115, which may facilitate operation of medical system 100 and may provide a more ergonomic position for the operator's hands. In other examples, medical device 101 may be directly coupled to working channel port 117 without mounting clamp 107, such as via a snap-fit coupler.

Handle portion 105 of medical device 101 may be moveable relative to a longitudinal axis E of handle portion 105, shown in FIG. 1A via arrows B and C. For example, handle portion 105 may pivot or tilt relative to a rotatable coupling assembly 203 (shown in FIG. 2A) and a proximal end (such as where actuator 201 is positioned) may move away from longitudinal axis E (shown via arrows B and C) in any lateral direction radially outward from longitudinal axis E. Handle portion 105 may include an energy port 111 configured to couple to a source of energy, such as electrical energy. Energy port 111 may be configured to provide energy to a cautery element 140, e.g. a wire/see FIG. 2B, of medical device 101. Handle portion 105 may also include an irrigation port 109 configured to provide access to an irrigation lumen 135 of medical device 101. Irrigation port 109 may be configured to couple to a source of fluid, such as a water or saline source. In some examples, irrigation port 109 may also be used as a suction port for aspiration purposes. In addition, handle portion 105 may include a guidewire port 112 configured to receive a guidewire and provide access to guidewire lumen 139. Handle portion 105 may also include one or more actuators 201, 209 for operating aspects of medical device 101. Actuators 201, 209 will be discussed in further detail below in relation to FIG. 2A.

FIG. 1B shows a cross-sectional view of insertion portion 103 at cross-section A. Insertion portion 103 may include articulation lumens 131, 133, an irrigation lumen 135, a cautery lumen 137, and a guidewire lumen 139. Each of articulation lumens 131, 133, irrigation lumen 135, cautery lumen 137, and guidewire lumen 139 may extend longitudinally through insertion portion 103 to distal end 104. Irrigation lumen 135 may be used for irrigation, suction, or irrigation/suction. Each articulation lumen 131, 133 may be configured to receive an articulation wire 141, 142; and articulation wires 141, 142 may be coupled to a distal portion of insertion portion 103 (for example, coupled to distal end 104) and may be movable within articulation lumens 131, 133. Articulation lumens 131, 133 may be positioned on opposing sides of insertion portion 103, such as positioned on opposing sides of a central longitudinal axis of insertion portion 103, and may be proximate to the radially-outermost surface 147 from a central longitudinal axis of insertion portion 103. In some examples, articulation lumens 131, 133 may be equidistant from a central longitudinal axis of insertion portion 103. Articulation wires 141, 142 may be made of any suitable material, such as stainless steel, Nitinol, or plastic. In other examples, articulation lumens 131, 133 may be configured to house bellows or any other flexible construction to achieve maneuverability of insertion portion 103. In some examples, bellows may be soft robotics used to actuate the maneuverability of insertion portion 103.

Irrigation lumen 135 may be configured to couple to a fluid source and may provide a means to deploy fluid from distal end 104 of insertion portion 103, and may also be configured to couple to a suction source (air suction source or vacuum) and may provide a means to apply suction from distal end 104 of insertion portion 103. Cautery lumen 137 may be configured to receive a cautery wire 140, and cautery wire 140 may be configured to receive energy and heat up in order to cauterize tissue of a patient. Cautery wire 140 may be configured to move within cautery lumen 137. Guidewire lumen 139 may be configured to receive a guidewire and may facilitate positioning of insertion portion 103 within a working channel of insertion portion 113. In other examples, insertion portion 113 may include three, four, five, or any other suitable number of articulation lumens 131, 133 for positioning articulation wires 141, 142. For example, insertion portion 103 may include four articulation lumens 131, 133 positioned equidistant from a central longitudinal axis of insertion portion 103, with each of the four articulation lumens 131, 133 positioned proximate to a radially-outermost surface 147 from a central longitudinal axis of insertion portion 103. In some examples, insertion portion 103 may include additional lumens for housing other components of medical device 101. In other examples, insertion portion 103 may not include one or more of articulation lumens 131, 133, irrigation lumen 135, cautery lumen 137, and guidewire lumen 139.

Figure 2A:
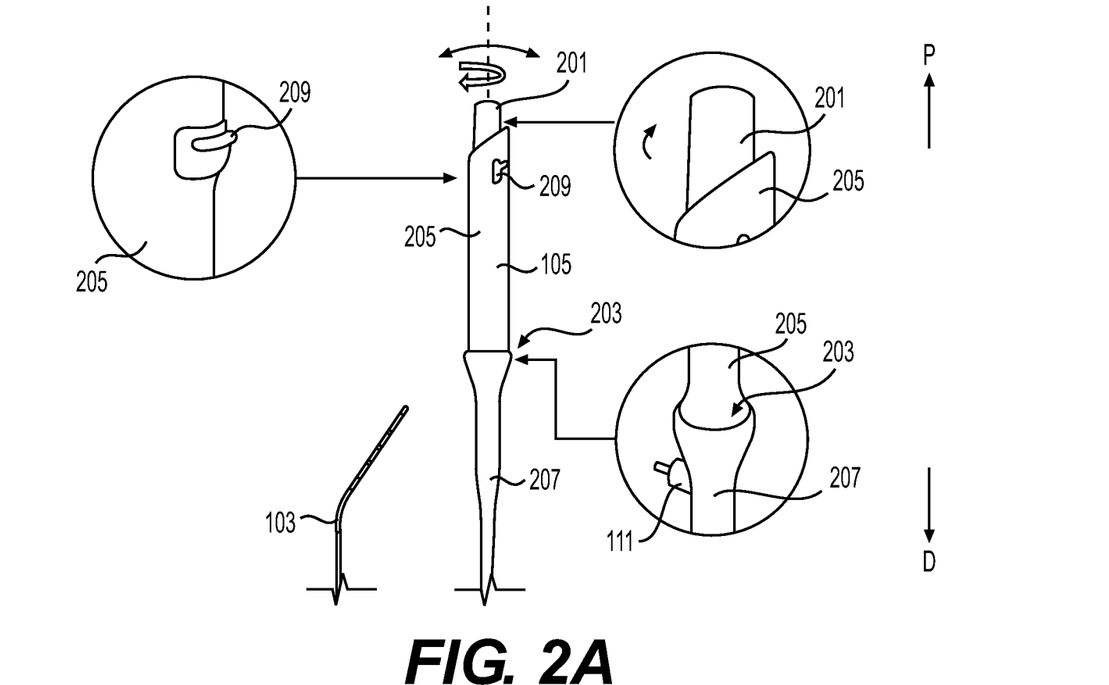
FIG. 2A illustrates a portion of an exemplary medical device of FIG. 1A, according to aspects of this disclosure.

FIG. 2A shows portions of medical device 101 including handle portion 105, insertion portion 103, and magnified views of portions of handle portion 105. Handle portion 105 may include a proximal portion 205 and a distal portion 207. Proximal portion 205 may be moveable relative to distal portion 207, and proximal portion 205 may be coupled to distal portion 207 via a rotatable coupling assembly 203. Rotatable coupling assembly 203 may be a hinge joint or ball and socket joint. Rotatable coupling assembly 203 may allow proximal portion 205 to rotate relative to distal portion 207 such that proximal portion 205 pivots about a point within rotatable coupling assembly 203. In some examples, rotatable coupling assembly 203 may be a ball joint and/or a frictional ball socket mechanism. Proximal portion 205 may pivot about rotatable coupling assembly 203 such that a proximal end of proximal portion 205 moves away from central longitudinal axis Z of medical device 101 while a distal end of proximal portion 205 remains aligned with central longitudinal axis Z. Rotatable coupling assembly 203 may provide a means for a user to move distal end 104 of insertion portion 103 via moving one or more articulation wires 141, 142.

Handle portion 105 may also include a first actuator 201 at proximal portion 205 of handle portion 105, such as at a proximal end of handle portion 105. First actuator 201 may be rotatable about longitudinal axis Z and may be configured to actuate movement of distal end 104 via one or more actuation wires 141, 142. First actuator 201 may be rotatable relative to proximal portion 205. In some examples, rotation of first actuator 201 may move both actuation wires 141, 142 in the proximal direction or the distal direction simultaneously to move distal end 104 upward or downward. In some examples, first actuator 201 may elevate distal end 104 and serve as an elevator actuator. Handle portion 105 may further include a second actuator 209. Second actuator 209 may be configured to turn on and off a supply of energy to cautery wire 140. In other examples, a separate actuator, such as a foot pedal or other button, may be configured to turn on and off a supply of energy to cautery wire 140. Second actuator 209 may be positioned at a proximal section of proximal portion 205 and may be a slideable and/or rotatable switch actuator. In some examples, second actuator 209 may be configured to actuate the distal end 104 and/or cautery wire 140. For example, rotation of second actuator 209 may actuate bending of cautery wire 140 to aid in cutting tissue.

In operation, medical system 100 may be used to conduct a medical operation within a body of a patient. Initially, insertion portion 113 of insertion device 102 may be inserted into the body of a patient, such as through an incision or a bodily orifice of the patient. Once insertion portion 113 is positioned at a target site within the body of the patient, the user may then insert insertion portion 103 of medical device 101 through working channel port 117 to position distal end 104 of insertion portion 103 proximate to the target site. In other examples, insertion portion 103 may be positioned within a working channel of insertion portion 113 prior to the user inserting insertion portion 113 into the body of the patient. Once both insertion portion 113 and insertion portion 103 are positioned at the target site, the user may then manipulate actuators 108 of insertion device 102 to move a distal portion of insertion portion 113. The user may also manipulate handle portion 105 of medical device 101 to move distal end 104 of insertion portion 103 independently of insertion portion 113. For example, the user may pivot proximal portion 205 relative to distal portion 207 of handle portion 105 to move distal end 104 to the right/left, and may rotate first actuator 201 to move distal end 104 upward/downward.

The user may also initiate cauterization using cautery wire 140 by actuating second actuator 209 or actuating a foot pedal actuator (not shown). For example, a user may move cautery wire 140 distally through cautery lumen 137 to deploy cautery wire 140 within the body of the patient, and then actuate second actuator 209 (or actuate a foot pedal actuator) to provide energy to cautery wire 140 and cauterize tissue. In other examples, distal end 104 may include an opening configured to allow cautery wire 140 to be exposed to the exterior of insertion portion 103 when distal end 104 is bent (shown in FIG. 2B). In some examples, the user may use one hand to hold handle portion 115 and actuate actuators 108 to move insertion portion 113; and may use the other hand to hold handle portion 105, actuate actuators 201, 209, and pivot proximal portion 205 relative to distal portion 207. Mounting clamp 107 may fix the position of distal portion 207 relative to handle portion 115, and may allow the user to pivot proximal portion 205 relative to distal portion 207 during operation. The user may also move insertion portion 103 distally and/or proximally to change the position of distal end 104. Medical device 101 may allow the user to: 1) pivot proximal portion 205 relative to distal portion 207 to move distal end 104 to the right or left; 2) actuate first actuator 201 to move distal portion 207 upwards or downwards; and 3) move insertion portion 103 distally or proximally relative to insertion portion 113 by pulling and/or pushing insertion portion 103 through a working channel of insertion portion 113. Accordingly, medical device 101 may provide the user with six degrees of movement of distal end 104 during a procedure. By providing means to move distal end 104 independently of the movement of insertion portion 113, medical system 100 may reduce procedure time, reduce unwanted movement of medical device 101, and reduce patient injuries during a procedure.

Figure 2B:
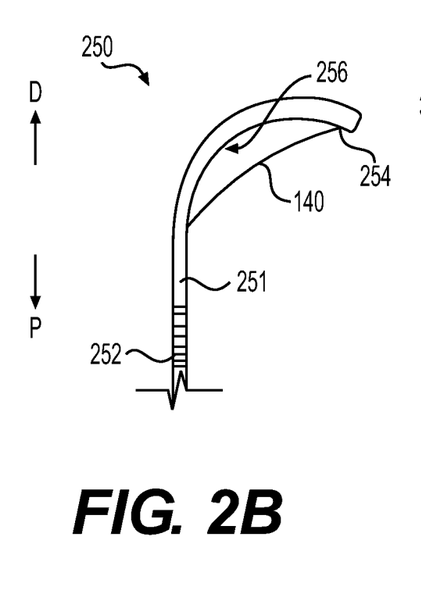
FIG. 2B illustrates a distal portion of an exemplary medical device, according to aspects of this disclosure.

FIG. 2B shows an exemplary distal portion 250 of an insertion portion 251 of a medical device, such as medical device 101. Distal portion 250 may be incorporated into any of the medical devices of this disclosure. Distal portion 250 may include an opening 256 configured to allow cautery wire 140 to be exposed to the exterior of insertion portion 251 when distal portion 250 is bent. Cautery wire 140 may be fixed to a distal end portion 254 of insertion portion 251, and opening 256 may allow cautery wire 140 to transition from being positioned within insertion portion 251 to being positioned outside of insertion portion 251 when distal portion 250 is bent. In some examples, distal portion 250 (or any other distal portion of a medical device described herein) may include a coil relief segment 252, which may facilitate the avoidance of kinking of distal portion 250 during operation. Coil relief segment 252 may be a biasing member such as a spring, a helically-wound wire, or any other suitable material. Coil relief segment 252 may be made of metal such as stainless steel, alloys such as nitinol, or any other material of suitable stiffness. In some examples, coil relief segment 252 may be coated with a heatsink material, a plastic extrusion, or any other suitable material.

Figure 3:
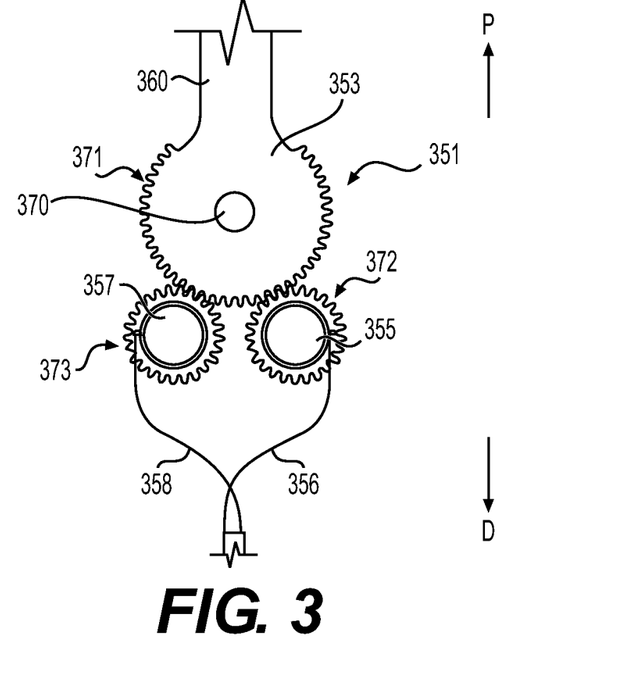
FIG. 3 is a side view of exemplary internal components of the medical device shown in FIG. 2A, according to aspects of this disclosure.

FIG. 3 shows an exemplary rotatable coupling assembly 351 which may be used in medical device 101. Rotatable coupling assembly 351 may be positioned within handle portion 105 and may provide a mechanism for moving articulation wires 356, 358. Articulation wires 356, 358 may be positioned within articulation lumens 131, 133. Rotatable coupling assembly 351 may include a rod 360 with a first gear 353 positioned at the distal end of rod 360. Rod 360 may extend longitudinally through an interior portion of proximal portion 205 of handle portion 105. In some examples, rotatable coupling assembly 351 may not include rod 360, and first gear 353 may be integrated into an interior portion of handle portion 105. As shown in FIG. 3, first gear 353 may be engaged with a second gear 355 and a third gear 357. Second gear 355 and third gear 357 may be positioned within distal portion 207 of handle portion 105. Articulation wire 356 may be coupled to second gear 355, and articulation wire 358 may be coupled to third gear 357. Rod 360 may be fixedly coupled to proximal portion 205 such that rod 360 moves when proximal portion 205 moves. Rod 360 may be configured to pivot about pivot point 370 when a user pivots proximal portion 205. When rod 360 pivots about pivot point 370, gear teeth 371 of first gear 353 engage gear teeth 372 of second gear 355 and gear teeth 373 of third gear 357 to rotate second gear 355 and third gear 357. The rotation of second gear 355 may move articulation wire 356 in the proximal or distal direction, such as by winding or unwinding articulation wire 356 from a portion of second gear 355. The rotation of third gear 357 may move articulation wire 358 in the proximal or distal direction, such as by winding or unwinding articulation wire 358 from a portion of third gear 357.

Figures 4A, 4B:
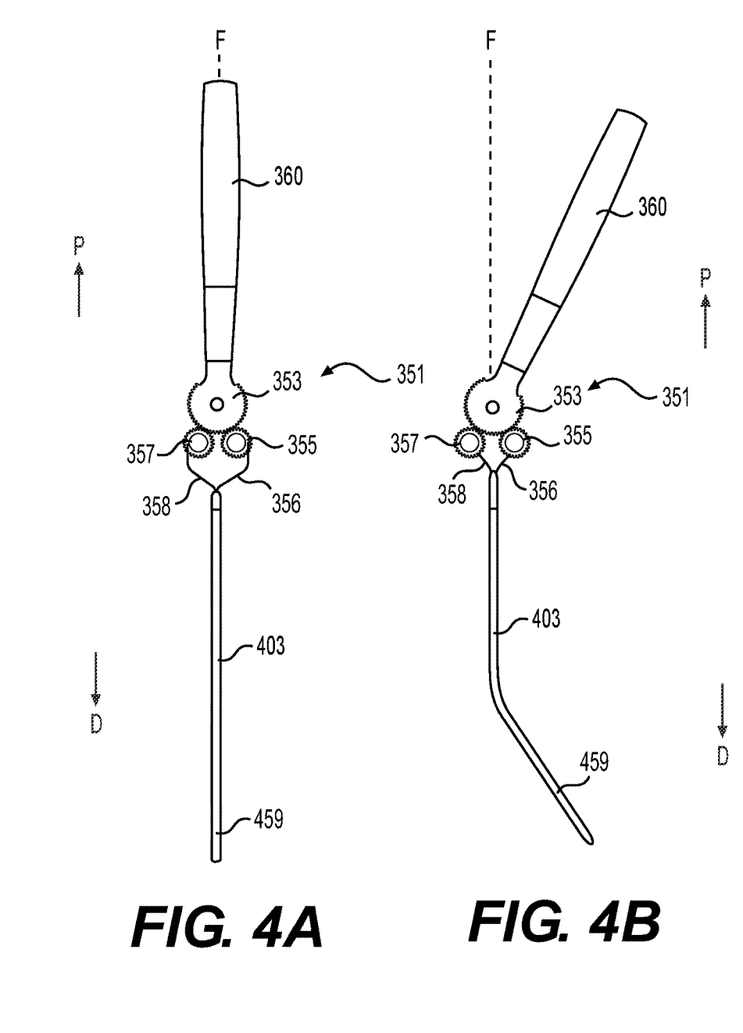
FIGS. 4A-4C illustrate the internal components of FIG. 3 in various positions, according to aspects of this disclosure.
Figure 4C:
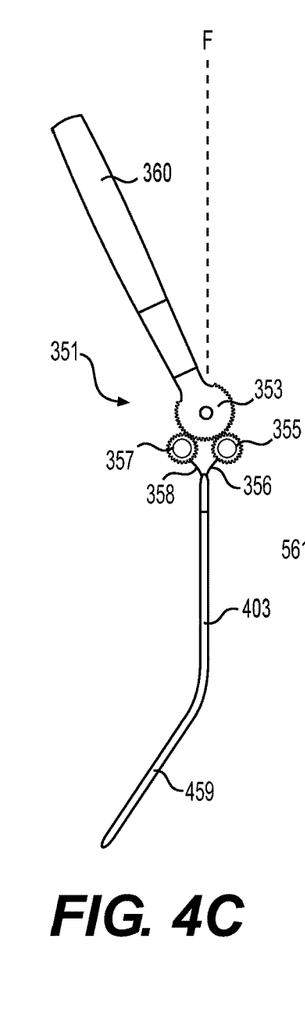

FIGS. 4A-4C show various positions of rotatable coupling assembly 351 and the resulting effect on an exemplary distal portion 459 of insertion portion 403, which may be used in medical device 101. FIG. 4A shows rotatable coupling assembly 351 in a neutral position with rod 360 aligned with longitudinal axis F. When in the neutral position shown in FIG. 4A, distal portion 459 is aligned with longitudinal axis F. As shown in FIG. 4B, when a user pivots rod 360 to the right (rotating gear 353 clockwise), actuation wire 356 is moved proximally via second gear 355 rotating counter-clockwise, actuation wire 358 is moved distally via third gear 357 rotating counter-clockwise, and distal portion 459 moves to the right of axis F. As shown in FIG. 4C, when a user pivots rod 360 to the left (rotating gear 353 counter-clockwise), actuation wire 358 is moved proximally via third gear 357 rotating clockwise, actuation wire 356 is moved distally via second gear 355 rotating clockwise, and distal portion 459 moves to the left of axis F. In some examples, a first actuator 201 of handle portion 105 may be rotated about axis Z to move the entire rotatable coupling assembly 351 upward or downward (along axis F shown in FIGS. 4A-4C) and may pull both actuation wires 356, 358 proximally to lift distal portion 459 upward or downward, creating an elevator action. In some examples, first actuator 201 may include a screw and knob mechanism for moving actuation wires 356, 358.

Figure 5:
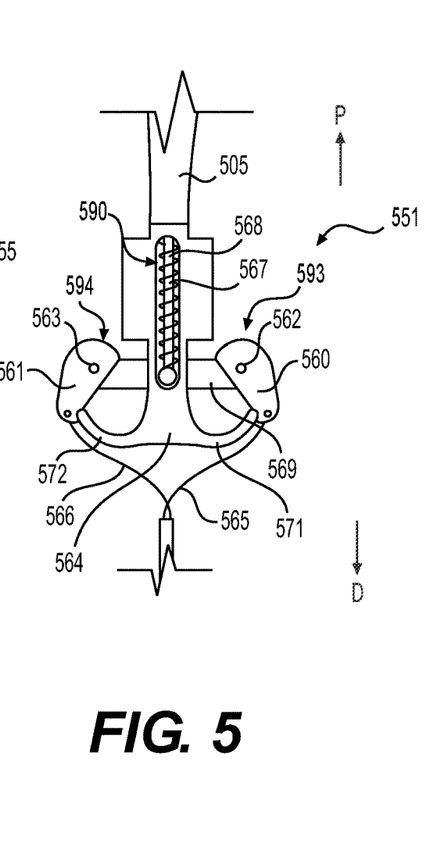
FIG. 5 is a side view of exemplary internal components of the medical device shown in FIG. 2A, according to another embodiment of this disclosure.

FIG. 5 shows another exemplary rotatable coupling assembly 551 which could be used in medical device 101. Rotatable coupling assembly 551 may be positioned within handle portion 105 and may provide a mechanism for moving articulation wires 565, 566. Articulation wires 565, 566 may be positioned within articulation lumens 131, 133. Rotatable coupling assembly 551 may include a rod 505 with a distal end 564 including two flanges 571, 572. Each flange 571, 572 may extend outward from a longitudinal axis of rod 505 and may curve upward towards the proximal direction. Rod 505 may extend longitudinally through an interior portion of proximal portion 205 of handle portion 105. In other examples, rotatable coupling assembly 551 may not include rod 505, and flanges 571, 572 may be integrated into proximal portion 205 of handle portion 105.

Rod 505 may include an internal cavity 590 configured to house an interior rod 567 and a biasing member 568. Interior rod 567 may be movable within rod 505 and biasing member 568 may be wound around interior rod 567.

In some examples, when first actuator 201 is rotated, interior rod 567 may move proximally to move rotatable coupling assembly 551 proximally, thereby pulling both articulation wires 565, 566 proximally and causing a distal portion of medical device 101 to move upward or downward. When first actuator 201 is released, biasing member 568 may return rotatable assembly 551 to a neutral position (shown in FIG. 5). A cross-bar 569 may be fixedly coupled to a distal end of interior rod 567 and may be moveable relative to rod 505. A first cam 560 may be rotatably coupled to a first end 593 of cross-bar 569, and a second cam 561 may be rotatably coupled to a second end 594 of cross-bar 569 that opposes the first end 593 of cross-bar 569. First cam 560 may be rotatable about pivot point 562, and second cam 561 may be rotatable about pivot point 563. Articulation wire 565 may be coupled to a distal portion of first cam 560, and articulation wire 566 may be coupled to a distal portion of second cam 561. Flange 571 may be configured to engage first cam 560 and flange 572 may be configured to engage second cam 561.

Figure 6A:
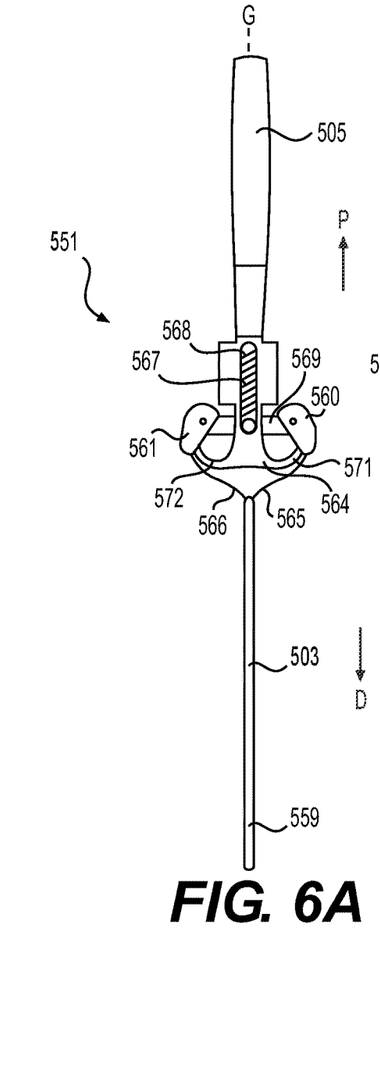
FIGS. 6A-6D illustrate the internal components of FIG. 5 in various positions, according to aspects of this disclosure.
Figure 6B:
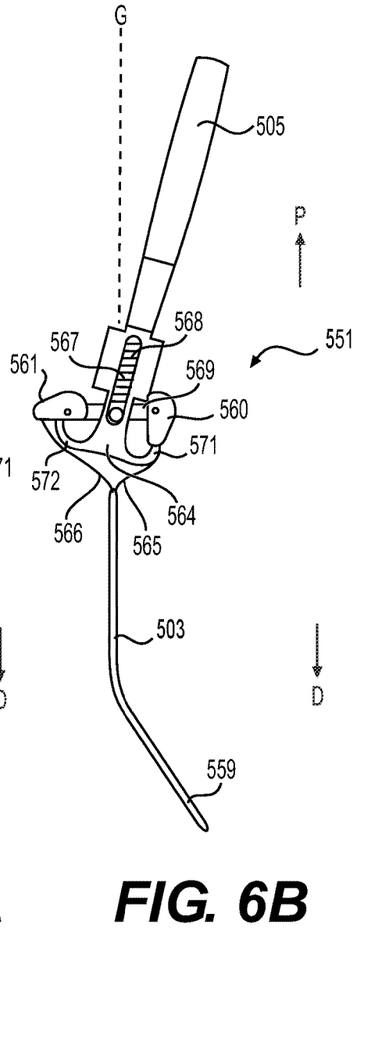
Figure 6C:
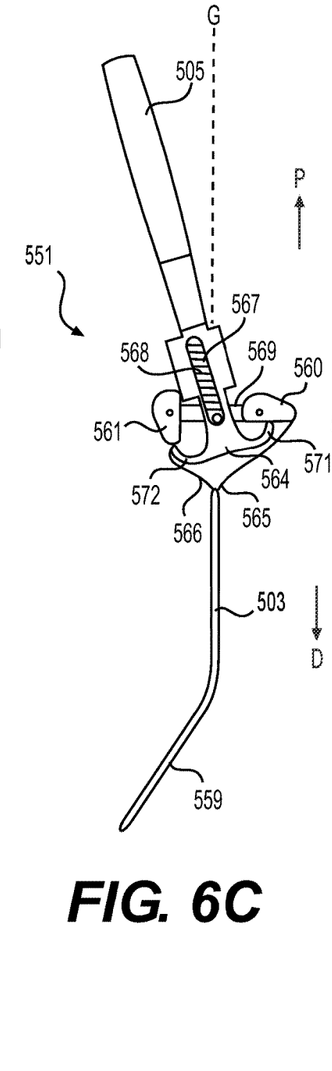

FIGS. 6A-6D show various positions of rotatable coupling assembly 551 and the resulting effect on an exemplary distal portion 559 of insertion portion 503, which could be used in medical device 101. FIG. 6A shows rotatable coupling assembly 551 in a neutral position with rod 505 aligned with longitudinal axis G. When in the neutral position shown in FIG. 6A, distal portion 559 is aligned with longitudinal axis G. As shown in FIG. 6B, when a user pivots rod 505 to the right, flange 572 pushes second cam 561 proximally, rotating second cam 561 clockwise about pivot point 563 to pull articulation wire 566 proximally, which results in distal portion 559 moving to the right of axis G. As shown in FIG. 6C, when a user pivots rod 505 to the left, flange 571 pushes first cam 560 proximally, rotating first cam 560 counter-clockwise about pivot point 562 to pull articulation wire 565 proximally, which results in distal portion 559 moving to the left of axis G.

Figure 6D:
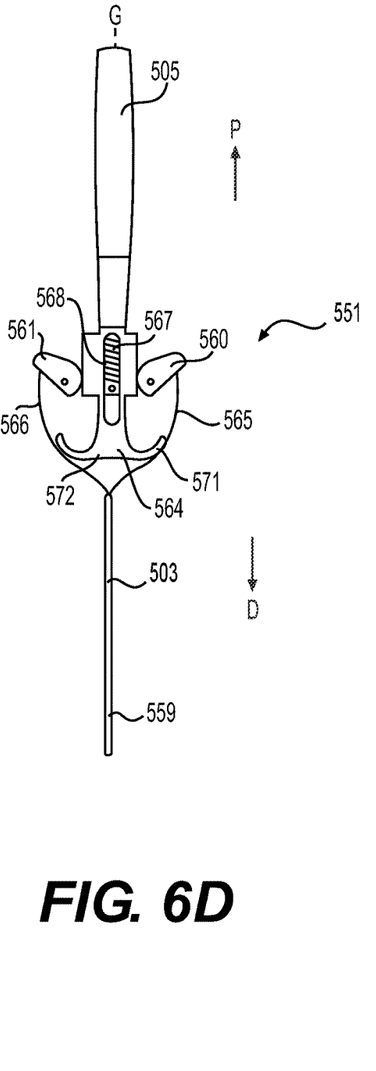

In some examples, interior rod 567 may be coupled to an actuator of handle portion 105, such as first actuator 201, and the actuator may be configured to move interior rod 567 proximally and distally. As shown in FIG. 6D, when interior rod 567 is moved proximally relative to rod 505 (and proximal portion 205 of handle portion 105), which may move cross-bar 569, first cam 560, second cam 561, and both articulation wires 565, 566 proximally. When both articulation wires 565, 566 are moved proximally simultaneously, distal portion 559 may be moved upward or downward. Biasing member 568 may bias interior rod 567 such that when a user releases the actuator that moved interior rod 567, interior rod 567 is moved via biasing member 568 to a neutral position (as shown in FIG. 6A).

Figure 7:
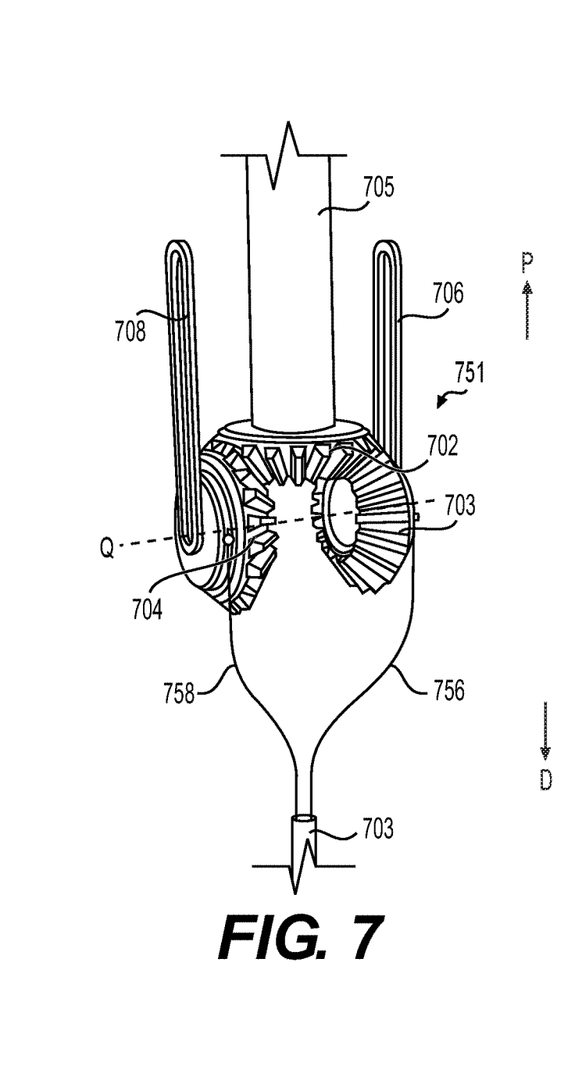
FIGS. 7 and 8 are side views of exemplary internal components of the medical device shown in FIG. 2A, according to another embodiment of this disclosure.
Figure 8:
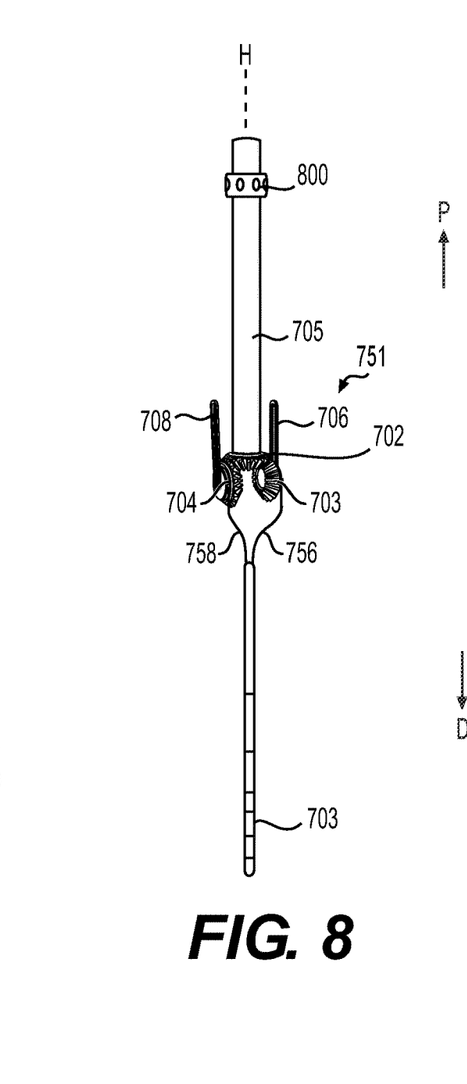

FIGS. 7 and 8 show another exemplary rotatable coupling assembly 751 which could be used in medical device 101. Rotatable coupling assembly 751 may be positioned within handle portion 105 and may provide a mechanism for moving articulation wires 756, 758. Articulation wires 756, 758 may be positioned within articulation lumens 131, 133. Rotatable coupling assembly 751 may include a rod 705 with a first gear 702 positioned at the distal end of rod 705. Rod 705 may extend longitudinally through an interior portion of proximal portion 205 of handle portion 105. As shown in FIG. 7, first gear 702 may be engaged with a second gear 703 and a third gear 704. Second gear 703 and third gear 704 may be positioned within distal portion 207 of handle portion 105. Articulation wire 756 may be coupled to second gear 703, and articulation wire 758 may be coupled to third gear 704. Rod 705 may be fixedly coupled to proximal portion 205 such that rod 705 moves when proximal portion 205 moves. In some examples, rotatable coupling assembly 751 may not include rod 705, and first gear 702 may be integrated into a proximal portion 205 of handle portion 105. Rod 705 may be configured to pivot about a pivot axis Q extending through the centers of second gear 703 and third gear 704 when a user pivots proximal portion 205. When rod 705 pivots about pivot axis Q, first gear 702 engages second gear 703 and third gear 704 to rotate second gear 703 and third gear 704 in either a clockwise or counter-clockwise direction simultaneously. Alternatively or additionally, rod 705 may also be configured to rotate about longitudinal axis H and cause first gear 702 to engage second gear 703 and third gear 704 to rotate second gear 703 in a clockwise direction and third gear 704 in a counter-clockwise direction simultaneously, or visversa, when rod 705 is rotated about longitudinal axis H in the opposite direction. Guide members 706, 708 may extend longitudinally parallel to axis H and may receive a portion of rotatable coupling assembly 751. Guide members 706, 708 may be fixedly coupled to handle portion 105, and may be configured to allow rotatable coupling assembly 751 to move proximally or distally through handle portion 105, for example when a user actuates first actuator 201 or actuator 800 to move rotatable coupling assembly 751 proximally or distally. In some examples, second gear 703 may be moveably coupled to guide member 706, and third gear 704 may be moveably coupled to guide member 708. In some examples, second gear 703 and third gear 704 may be moveably coupled to guide members 706, 708 such that second gear 703 and third gear 704 each move within a slot or lumen of guide member 706 and guide member 708, respectively.

Articulation wire 756 may be coupled to second gear 703 at a position on the opposite side of axis Q from the position articulation wire 758 may be coupled to third gear 704. By positioning and fixing articulation wires 756, 758 on opposite sides of axis Q, articulation wire 756 may move distally when second gear 703 is rotated clockwise, and articulation wire 758 may move proximally when third gear 704 is rotated clockwise. Accordingly, when a user pivots rod 705 about axis Q to move second gear 703 and third gear 704 simultaneously clockwise, articulation wire 756 may move distally and articulation wire 758 may move proximally. This mechanism may allow a user to move a distal portion of insertion portion 703 to the right or left in a similar manner as described hereinabove with relation to rotatable coupling assemblies 351, 551. When a user rotates rod 705 about longitudinal axis H, both articulation wires 756, 758 may move proximally from second gear 703 and third gear 704 rotating in opposite directions. When a user rotates rod 705 about longitudinal axis H, a distal portion of insertion portion 703 may move upward from both articulation wires 756, 758 moving proximally, in the same manner described hereinabove in relation to FIG. 6D.

Figure 9:
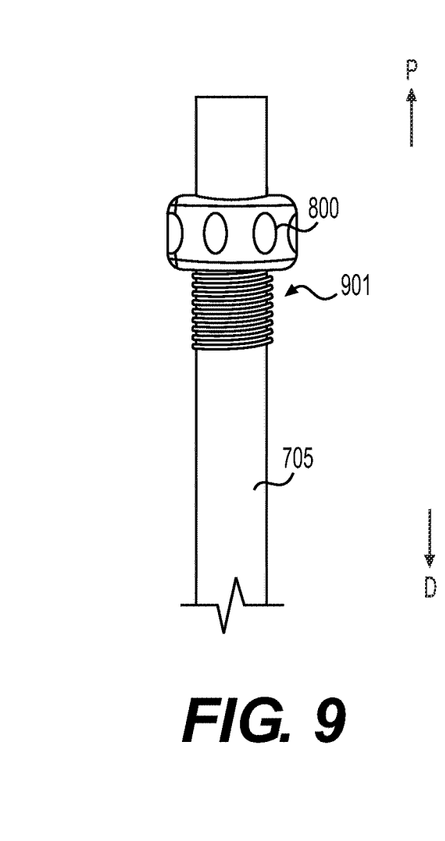
FIG. 9 is a side view of a portion of the internal components shown in FIGS. 7 and 8, according to aspects of this disclosure.

In some examples, actuator 800 may be a screw actuator that rotates within threads 901 of rod 705. Actuator 800 may be configured to move rotatable assembly 751 proximally or distally via rotation of actuator 800. In some examples, actuator 800 may be exposed, exterior to handle portion 105.

Figure 10:
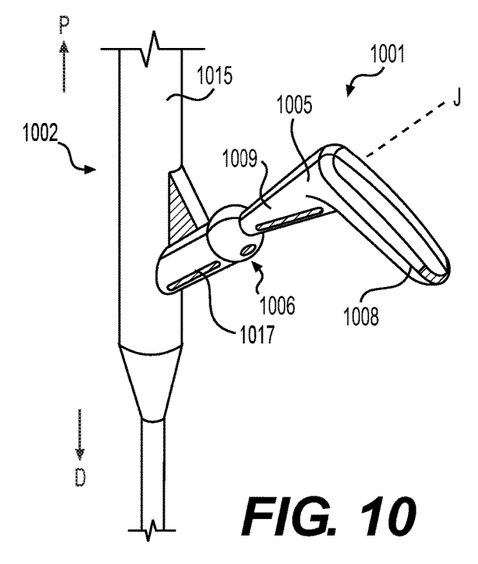
FIG. 10 illustrates a portion of an exemplary medical system including two medical devices in a coupled configuration, according to aspects of this disclosure.
Figure 11:
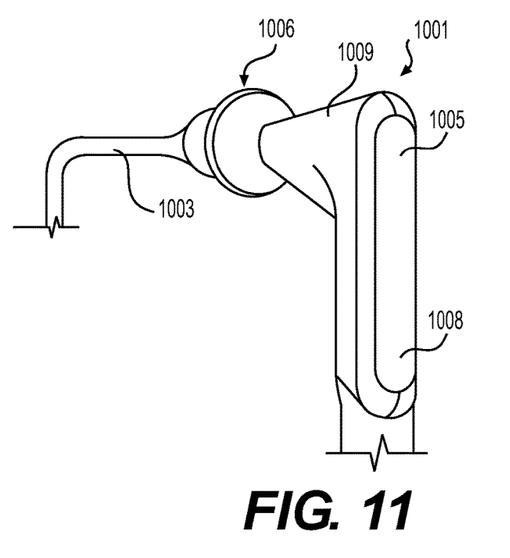
FIG. 11 illustrates a portion of an exemplary medical device of FIG. 10, according to aspects of this disclosure.

FIG. 10 shows a proximal portion of an alternative embodiment of a medical device 1001 coupled to a handle portion 1015 of an insertion device 1002. Insertion device 1002 and medical device 1001 may have any of the features described hereinabove with regard to insertion device 102 and medical device 101. As shown in FIG. 11, medical device 1001 may include an insertion portion 1003, a rotatable coupling assembly 1006, and a handle portion 1005. Handle portion 1005 may include any of the components of other handle portions described in this disclosure. Handle portion 1005 may be L-shaped and may include a lateral portion 1008 and a distal portion 1009. Distal portion 1009 may be aligned with longitudinal axis J of medical device 1001, and lateral portion 1008 may extend from a proximal end of distal portion 1009 radially outward from longitudinal axis J. Rotatable coupling assembly 1006 may be configured to directly couple to working channel port 1017 of handle portion 1015. Lateral portion 1008 may be configured for a user to hold during operation. Once coupled to working channel port 1017 of handle portion 1015, a user may rotate handle portion 1005 relative to handle portion 1015 to pivot handle portion 1005 about rotatable coupling assembly 1006, which may cause a distal portion of insertion portion 1003 to move right, left, upward, or downward. In some examples, rotatable coupling assembly 1006 may include a ball socket that has a friction fit, which may allow a user to release handle portion 1005 during operation and maintain the position of medical device 1001 without having to hold handle portion 1005. In some examples, rotatable coupling assembly 1006 may be configured to snap-fit onto working channel port 1017.

Figure 12:
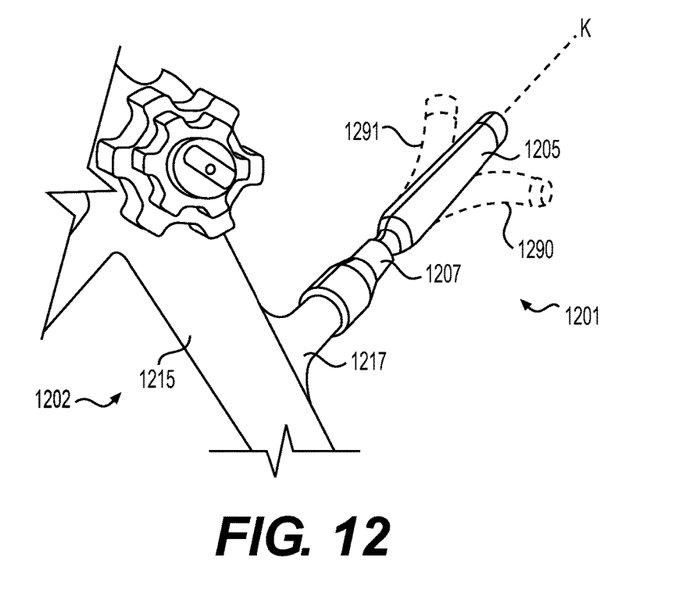
FIG. 12 illustrates a portion of an exemplary medical system including two medical devices in a coupled configuration, according to aspects of this disclosure.

FIG. 12 shows an alternative embodiment of a medical device 1201 coupled to a handle portion 1215 of an insertion device 1202. Insertion device 1202 and medical device 1201 may have any of the features described hereinabove with regard to insertion devices 102, 1002 and medical devices 101, 1001. Medical device 1201 may include handle portion 1205, coupling portion 1207, and an insertion portion (not shown). Handle portion 1205 may include any of the components of the other handle portions described in this disclosure. Handle portion 1205 may be cylindrical and may be made of a flexible mesh material configured to bend when a user moves handle portion laterally relative to central longitudinal axis K of medical device 1201. In other examples, handle portion 1205 may be made of any other flexible material. Coupling portion 1207 may be configured to fixedly coupled handle portion 1205 to working channel port 1217 of handle portion 1215. For example, coupling portion 1207 may be configured to snap fit onto working channel port 1217. In operation, a user may bend handle portion 1205 laterally relative to central longitudinal axis K (shown in dotted-lines as bent handle portions 1290, 1291 in FIG. 12) to move articulation wires of medical device 1201 and move a distal portion of the insertion portion of medical device 1201. For example, a user may bend handle portion 1205 to the right to move a distal portion of insertion portion to the right, and may bend handle portion 1205 to the left to move a distal portion of insertion portion to the left. In some examples, medical device 1201 may allow a user to move an insertion portion to the right, left, upward, downward, and/or diagonal directions.

Figure 13:
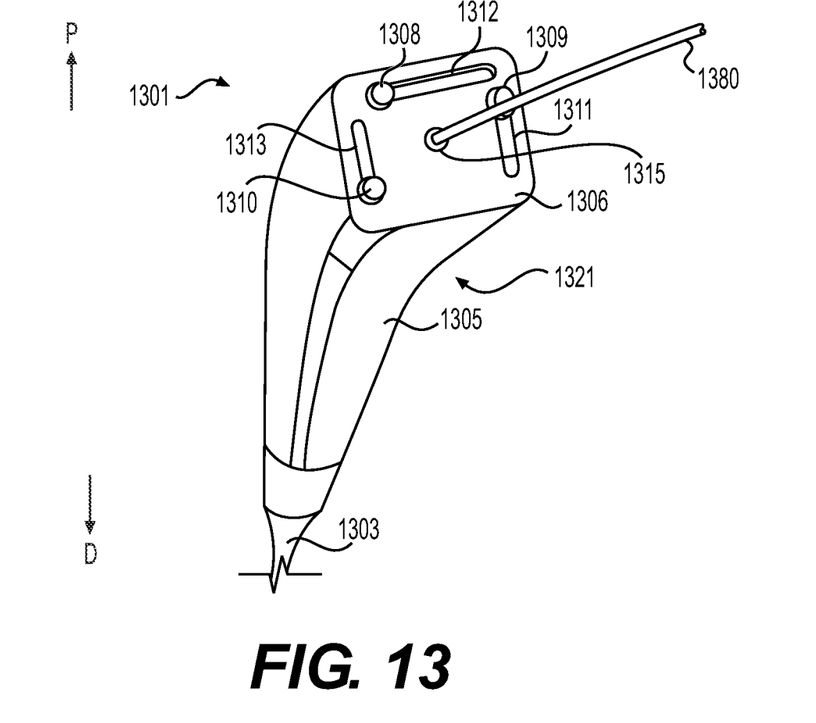
FIG. 13 illustrates a portion of an exemplary medical device, according to aspects of this disclosure.

FIG. 13 shows a proximal portion of another alternative embodiment of a medical device 1301 configured to be inserted into a working channel of an insertion device 102, 1002, 1202. Medical device 1301 may have any of the features described hereinabove with regard to medical devices 101, 1001, 1201. Medical device 1301 may include handle portion 1305 and an insertion portion 1303. Handle portion 1305 may include any of the components of other handle portions described in this disclosure. Handle portion 1305 may be approximately rectangular in cross-section and may include a curved portion 1321 and a proximal-facing, approximately rectangular surface 1306. Curved portion 1321 may be configured to allow the user to access proximal-facing surface 1306 using the user's thumb while holding handle portion 1305. Proximal facing surface 1306 may be planar and may be angled relative to a central longitudinal axis of medical device 1301. Three actuators 1308, 1309, 1310 may be positioned on proximal-facing surface 1306. In other examples, one, two, four, five, or any other suitable number of actuators may be present on proximal-facing surface 1306. Each actuator 1308, 1309, 1310 may be a knob positioned within a groove 1312, 1311, 1313, respectively, of proximal-facing surface 1306, and may be configured to move within the groove 1312, 1311, 1313. A guidewire lumen opening 1315 may also be positioned on proximal-facing surface 1306. Guidewire lumen opening 1315 may be positioned at a center portion of proximal-facing surface 1306 and may provide access to a guidewire lumen that extends longitudinally through insertion portion 1303. Guidewire lumen opening 1315 may be configured to receive a guidewire 1380.

Any of actuators 1308, 1309, 1310 may be used to move a distal portion of insertion portion 1303 in the right-left directions, in the upward and downward directions, in diagonal directions, and/or to bend a distal portion of insertion portion 1303. In some examples, an actuator 1308, 1309, 1310 may be configured to bend a distal portion of insertion portion 1303 to deploy a cautery wire 140. In some examples, actuator 1310 may be configured to move a distal portion of insertion portion 1303 upward or downward relative to a central longitudinal axis of medical device 1301 via movement of actuator 1310 within groove 1313. Actuator 1308 may be configured to move a distal portion of insertion portion 1303 in a right or left direction via movement of actuator 1308 within groove 1312, and actuator 1309 may be configured to bend a distal portion of insertion portion 1303 via movement of actuator 1309 within groove 1311. In some examples, bending a distal portion of insertion portion 1303 may cause a cautery wire 140 to be exposed exterior to insertion portion 1303. In other examples, one or more of actuators 1308, 1309, 1310 may be configured to actuate any other feature of medical device 1301, such as initiating the supply of energy to a cautery wire 140. By positioning actuators 1308, 1309, 1310 on proximal-facing surface 1306, handle portion 1305 may provide an ergonomic way for a user to actuate each actuator 1308, 1309, 1310 using only one hand. In some examples (not shown), handle portion 1305 may include a snap-fit coupler to couple handle portion 1305 to a working channel port 117, 1017, 1217 of an insertion device 102, 1002, 1202. In other examples, handle portion 1305 may be coupled to an insertion device 102, 1002, 1202 using a mounting clamp 107.

In operation, a user may move one or more of actuators 1308, 1309, 1310 within grooves 1311, 1312, 1313 to move a distal portion of the insertion portion 1303 of medical device 1301. For example, a user may actuate actuator 1310 by sliding actuator 1310 within groove 1313 to move a distal portion of insertion portion 1303 in an upward or downward direction. In some examples, medical device 1301 may allow a user to move an insertion portion to the right, left, upward, downward, and/or diagonal directions.

Figure 14:
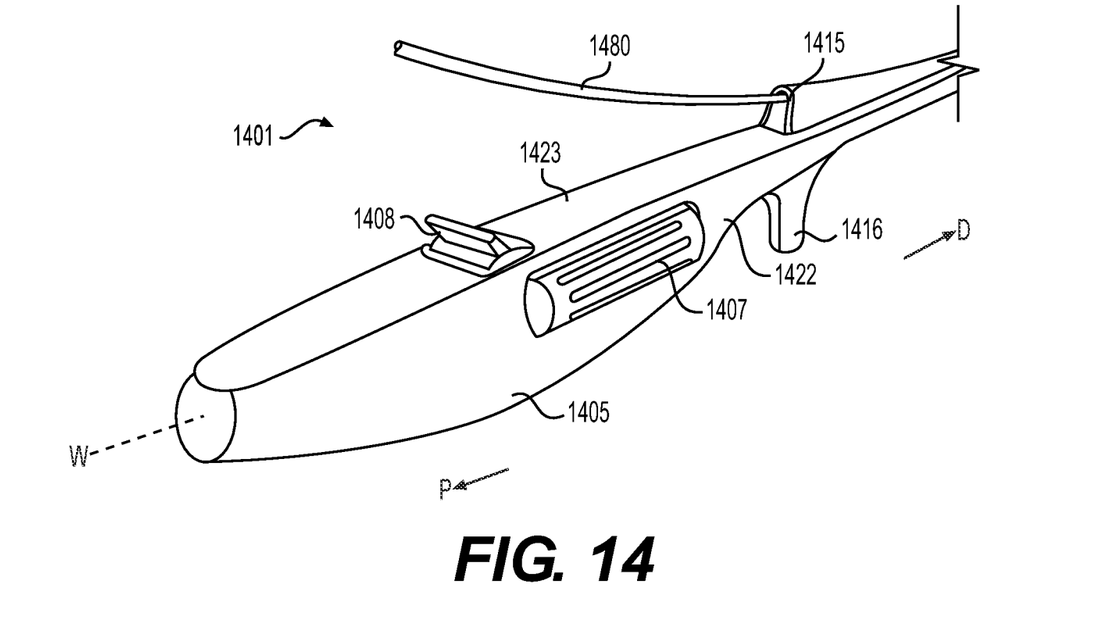
FIG. 14 illustrates a portion of an exemplary medical device, according to aspects of this disclosure.

FIG. 14 shows a proximal portion of an alternative embodiment of a medical device 1401 configured to be inserted into a working channel of an insertion device 102, 1002, 1202. Medical device 1401 may have any of the features described hereinabove with regard to medical devices 101, 1001, 1201, 1301. Medical device 1401 may include handle portion 1405 and an insertion portion (not shown). Handle portion 1405 may include any of the components of other handle portions described in this disclosure. Handle portion 1405 may include a curved surface 1422 and a planar surface 1423, and together the curved surface 1422 and the planar surface 1423 may extend circumferentially around a central longitudinal axis W of medical device 1401. Curved surface 1422 may be configured to conform to a user's hand, e.g. palm. A lever 1408 may be positioned on planar surface 1423 and may be configured to be actuated via a user's thumb. A rotating knob 1407 may be positioned on the curved surface 1422 and may be proximate to lever 1408. Rotating knob 1407 may be cylindrical and may be longitudinally aligned with longitudinal axis W. Rotating knob 1407 may include ridges extending longitudinally on an exterior surface of rotating knob 1407. Lever 1408 and rotating knob 1407 may be configured to actuate movement of a distal portion of the insertion portion of medical device 1401, such as moving a distal portion of insertion portion in a right-left direction, an upward or downward direction, or bending a distal portion of the insertion portion. Handle portion 1405 may also include a cautery input 1416 configured to receive energy from an energy source and supply energy to a cautery wire 140. A guidewire port 1415 may be positioned at a proximal portion of handle portion 1405 and may be configured to receive a guidewire 1480. Guidewire port 1415 may provide access to a guidewire lumen of the insertion portion of medical device 1401.

To operate medical device 1401, a user may hold handle portion 1405 such that the user's thumb is proximate to lever 1408 and knob 1407. In some examples, the user may rotate knob 1407 to move a distal portion of the insertion portion to the right or left direction, and may also move lever 1408 to move a distal portion of the insertion portion upward or downward.

While principles of this disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:
1. A medical system comprising:
a first medical device including a first handle, the first handle including a proximal portion and a distal portion, wherein the proximal portion pivots relative to the distal portion;
a rotatable coupling assembly coupling the proximal portion and the distal portion of the first handle;
a second medical device including a second handle;
a mounting clamp configured to couple the second handle to the first handle;
an insertion portion coupled to the distal portion of the first handle and configured to be positioned within a body lumen;
an articulation wire and a cautery wire extending from the first handle through the insertion portion;
wherein the articulation wire is a first articulation wire, and wherein the rotatable coupling assembly includes:
a rod fixedly coupled to the proximal portion of the first handle and configured to pivot about a pivot point;
a first gear at a distal end of the proximal portion of the first handle;
a second gear engaged with the first gear, wherein the first articulation wire is coupled to the second gear; and
a third gear engaged with the first gear, wherein a second articulation wire is coupled to the third gear;
wherein, as the rod pivots about the pivot point, the first gear engages the second gear and the third gear to move the articulation wire and a distal portion of the insertion portion;
a first actuator positioned on the first handle, wherein pivoting the first actuator relative to the proximal portion of the first handle moves a distal end of the insertion portion in an upward direction and a downward direction; and
a second actuator positioned at the proximal portion of the first handle, wherein the second actuator is configured to actuate the cautery wire to aid in cutting;
wherein pivoting of the proximal portion of the first handle relative to the distal portion of the first handle moves the first articulation wire and the second articulation wire relative to the insertion portion to bend a distal portion of the insertion portion.

2. The medical system of claim 1,
wherein the second articulation wire is configured to move the distal portion of the insertion portion when the first actuator is actuated.

3. The medical system of claim 1, wherein the mounting clamp includes a first clamp, a second clamp, and an arm extending between the first clamp and second clamp, wherein the arm is configured to space the first handle from the second handle, wherein the mounting clamp fixes a position of the distal portion relative to the second handle of the second medical device.

4. The medical system of claim 1, wherein the insertion portion includes an irrigation lumen, a guidewire lumen, and a cautery lumen accommodating the cautery wire.

5. The medical system of claim 1, wherein the first handle is coupled to the insertion portion via the rotatable coupling assembly.

6. The medical system of claim 5,
wherein rotation of the second gear or the third gear moves the first articulation wire in a proximal or a distal direction.

7. The medical system of claim 5, wherein the rotatable coupling assembly is a ball and socket joint.

8. The medical system of claim 5, wherein the rotatable coupling assembly includes a rod, wherein the rod extends longitudinally through an interior portion of the proximal portion of the first handle.

9. The medical system of claim 8, wherein the rod is fixedly coupled to the proximal portion of the first handle such that the rod moves when the proximal portion moves.

10. The medical system of claim 1, wherein the proximal portion of the first handle pivots such that a proximal end of the proximal portion moves away from a central longitudinal axis of the first handle and a distal end of the proximal portion remains aligned with the central longitudinal axis.

11. The medical system of claim 1, wherein the first actuator is rotatable about a longitudinal axis to actuate movement of a distal end of the distal portion.

12. The medical system of claim 1, wherein the first actuator and the second actuator are positioned on the proximal portion of the first handle, wherein the second actuator is distal to the first actuator.

13. The medical system of claim 1, wherein the second actuator is a rotatable switch actuator, wherein rotation of the second actuator is configured to bend the cautery wire.

14. The medical system of claim 1, wherein the distal portion of the insertion portion includes an opening configured to allow the cautery wire to be exposed to an exterior of the insertion portion when the distal portion of the insertion portion is bent.

15. A medical device comprising:
a handle including a proximal portion and a distal portion;
a rotatable coupling assembly coupling the proximal portion and the distal portion of the handle;
an insertion portion coupled to the distal portion of the handle and configured to be positioned within a body lumen;
wherein the rotatable coupling assembly includes:
a rod extending longitudinally through an interior portion of the proximal portion of the handle and configured to pivot about a pivot point;
a first gear at a distal end of the proximal portion of the handle;
a second gear engaged with the first gear, wherein a first articulation wire is coupled to the second gear; and
a third gear engaged with the first gear, wherein a second articulation wire is coupled to the third gear;
wherein, as the rod pivots about the pivot point, the first gear engages the second gear and the third gear to move the articulation wire and a distal portion of an insertion portion; and
an articulation wire and a cautery wire extending from the handle through the insertion portion;
wherein pivoting the proximal portion of the handle relative to the distal portion of the handle moves the first articulation wire and the second articulation wire relative to the insertion portion to bend a distal portion of the insertion portion.

16. The medical device of claim 15, wherein the rod is fixedly coupled to the proximal portion of the handle such that the rod moves when the proximal portion moves.

17. The medical device of claim 15, wherein a first actuator is positioned on the handle, wherein pivoting the first actuator relative to the proximal portion of the handle moves the distal portion of the insertion portion upward and downward.

18. The medical device of claim 17, further comprising a second actuator positioned on the handle, wherein the second actuator is configured to actuate the cautery wire to aid in cutting.

19. A medical device comprising:
a handle including a proximal portion and a distal portion;
a rotatable coupling assembly coupling the proximal portion and the distal portion of the handle;
an insertion portion coupled to the distal portion of the handle and configured to be positioned within a body lumen;
an articulation wire and a cautery wire extending from the handle through the insertion portion;
wherein the articulation wire is a first articulation wire, and
wherein the rotatable coupling assembly includes:
a rod fixedly coupled to the proximal portion of the handle and configured to pivot about a pivot point;
a first gear at a distal end of the proximal portion of the handle;
a second gear engaged with the first gear, wherein the first articulation wire is coupled to the second gear; and
a third gear engaged with the first gear, wherein a second articulation wire is coupled to the third gear;
wherein, as the rod pivots about the pivot point, the first gear engages the second gear and the third gear to move the articulation wire and a distal portion of the insertion portion.

20. The medical device of claim 19, wherein a first actuator is positioned on the handle, wherein pivoting the first actuator relative to the proximal portion of the handle moves the distal portion of the insertion portion upward and downward, wherein a second actuator positioned at the proximal portion of the handle, and wherein the second actuator is configured to actuate the cautery wire to aid in cutting.

* * * * *